(12) United States Patent
Ganesan et al.

(10) Patent No.: US 7,377,170 B2
(45) Date of Patent: May 27, 2008

(54) SYSTEM AND METHOD FOR THE IDENTIFICATION OF CHEMICAL MECHANICAL PLANARIZATION DEFECTS

(75) Inventors: Rajesh Ganesan, Tampa, FL (US); Tapas K. Das, Tampa, FL (US); Arun K. Sikder, Tampa, FL (US); Ashok Kumar, Tampa, FL (US)

(73) Assignee: University of South Florida, Tampa, FL (US)

( * ) Notice: Subject to any disclaimer, the term of this patent is extended or adjusted under 35 U.S.C. 154(b) by 28 days.

(21) Appl. No.: 11/554,716

(22) Filed: Oct. 31, 2006

(65) Prior Publication Data

US 2007/0061088 A1  Mar. 15, 2007

Related U.S. Application Data

(63) Continuation-in-part of application No. 10/907,633, filed on Apr. 8, 2005, now abandoned.

(60) Provisional application No. 60/521,357, filed on Apr. 8, 2004.

(51) Int. Cl.
*G01N 29/00* (2006.01)

(52) U.S. Cl. .......................... 73/587; 73/602

(58) Field of Classification Search ................. 73/587, 73/596–600, 602; 451/1, 5, 8, 10, 11, 41, 451/159, 285, 287; 438/10, 14; 702/56, 702/183–184, 33–35

See application file for complete search history.

(56) References Cited

U.S. PATENT DOCUMENTS

| | | | | | |
|---|---|---|---|---|---|
| 5,253,530 | A | * | 10/1993 | Letcher, III | 73/602 |
| 5,723,791 | A | * | 3/1998 | Koch et al. | 73/597 |
| 6,397,679 | B1 | * | 6/2002 | Sadok et al. | 73/596 |
| 6,424,137 | B1 | * | 7/2002 | Sampson | 324/76.21 |
| 6,431,953 | B1 | * | 8/2002 | Carter et al. | 451/5 |
| 6,585,562 | B2 | * | 7/2003 | Gitis et al. | 451/5 |
| 6,640,632 | B1 | * | 11/2003 | Hatanaka et al. | 73/598 |
| 6,675,106 | B1 | * | 1/2004 | Keenan et al. | 702/28 |
| 6,709,314 | B2 | * | 3/2004 | Kaushal et al. | 451/8 |
| 6,957,581 | B2 | * | 10/2005 | Gilgunn | 73/587 |
| 6,971,944 | B2 | * | 12/2005 | Berman et al. | 451/5 |
| 7,008,299 | B2 | * | 3/2006 | Chandrasekaran | 451/41 |

* cited by examiner

*Primary Examiner*—Helen Kwok
(74) *Attorney, Agent, or Firm*—Molly L. Sauter; Smith & Hopen, P.A.

(57) ABSTRACT

The present invention presents a novel application of a wavelet-based multiscale method in a nanomachining process chemical mechanical planarization (CMP) of wafer fabrication. The invention involves identification of delamination defects of low-k dielectric layers by analyzing the nonstationary acoustic emission (AE) signal collected during copper damascene (Cu-low k) CMP processes. An offline strategy and a moving window-based strategy for online implementation of the wavelet monitoring approach are developed.

20 Claims, 10 Drawing Sheets

SYSTEM AND METHOD FOR THE IDENTIFICATION OF CHEMICAL MECHANICAL PLANARIZATION DEFECTS

CROSS REFERENCE TO RELATED APPLICATIONS

This application is a continuation-in-part of and claims priority to currently pending U.S. patent application Ser. No. 10/907,633, entitled, "System and Method for the Identification of Chemical Mechanical Planarization Defects", filed Apr. 8, 2005, which claims priority to U.S. Provisional Patent Application No. 60/531,357, entitled, "Method of Identifying Defects in Chemical Mechanical Planarization", filed Apr. 8, 2004.

BACKGROUND OF THE INVENTION

Some of the critical requirements facing semiconductor device manufacturing are continual feature-size reduction, introduction of new materials for higher processing speeds and improved reliability, multilevel metallization (MLM), or interconnections, and increased productivity through larger wafer sizes. Wafer polishing using chemical mechanical planarization (CMP) is a key nanoscale manufacturing step that can significantly impact how the above requirements are met by the industry. However, the increased sophistication of the CMP process has brought difficult manufacturing challenges including the identification of defects such as delamination, dishing, under/over polishing, process monitoring, and process control.

Industrial practices currently used in the art for the identification of delamination defects suggests offline methods such as noncontact capacitance probe measurements, photothermal techniques, and examination of finished wafers under optical and scanning electron microscopy (SEM). However, such offline methods do not provide real-time information that can be used to improve productivity and implement online process monitoring and control. Moreover, offline analysis also increases cost of ownership. Currently there are no efficient in situ tools and detailed implementable procedures known in the art to detect delamination defects.

In recent years, acoustic emission (AE) technology has emerged as a viable means to examine and characterize chemical mechanical planarization (CMP) processes. The AE signal arising out of the CMP process, where material removal takes place at the nanoscale level, has a very high signal to noise ratio and, as such, a high sensitivity. Also, the frequency of the AE signal is very high compared to those of machine vibrations and other environmental noises and, thus, provides a good representation of the material removal process of planarization. The above properties of the AE signal make it very suitable in extracting critical information about the state of the CMP process and in building detection and control strategies.

The acoustic emission signal is nonstationary and its strength, measured in volts, is high at the beginning of the CMP process and subsides as polishing progresses. The signal spans over a broad range of high frequencies and contains an abundance of time-based characteristics and noise. Consequently, visual inspection of time plots of AE signals fails to provide any meaningful information. Thus, to extract meaningful information from the acoustic emission signal, a systematic time-frequency analysis is required.

Acoustic emission signal analysis techniques known in the art include time-domain methods involving descriptors such as peak level, root-mean-square (RMS) value, crest factor, kurtosis analysis, and pulse count. These conventional time-domain analysis methods are sensitive to impulsive oscillations, but have limited utility in extracting hidden patterns and frequency related information in the AE signals. It is known in prior art that this problem is partially overcome by spectral (frequency) analysis such as Fourier transform, the power spectral density, and the coherence function analysis. However, many spectral methods rely on the implicit fundamental assumption of signals being periodic and stationary and are also inefficient in extracting time related features. Moreover, Fourier transform of nonstationary signals results in averaging of the frequency components over the entire duration of the signal. This problem has been addressed to a large extent through the use of short time Fourier transform (STFT) methods. However, this method uses a fixed tiling scheme, i.e., it maintains a constant aspect ratio (the width of the time window to the width of the frequency band) throughout the analysis. As a result, one must choose multiple window widths to analyze different data features localized in time and frequency domains. Hence, the STFT is badly adapted to signals where patterns with different scales appear, and it resolves short time phenomena associated with high frequencies poorly. In recent years, time-frequency methods, such as wavelet-based multiresolution analysis have gained popularity in analysis of both stationary and nonstationary signals. These methods provide excellent time-frequency localized information, which is achieved by varying the aspect ratio. Hence, time and frequency localized features are analyzed simultaneously with high resolution and the scheme is more adaptable to transient signals.

It is known in prior art that wavelet analysis could be used to process acoustic emission but no detailed step-by-step procedure that can implement both in-situ and ex-situ has been presented. Accordingly, what is needed in the art is a systematic wavelet-based time-frequency approach having the potential to analyze nonstationary acoustic emission signals and provide useful insight into the chemical mechanical planarization process for the purpose of identifying defects both online (in-situ) and offline (ex-situ) as required.

SUMMARY OF INVENTION

The present invention addresses the problem of online detection of delamination defects that occur in the chemical mechanical planarization (CMP) process of wafer fabrication in semiconductor manufacturing. Delamination is a commonly occurring defect in the wafer fabrication process, which causes significant loss in productivity. Since such defects are only visible under a powerful microscope, such as a Scanning Electron Microscope (SEM), often these defects are not detected until the final testing phase of the wafer circuitry, thus resulting in significant losses from the standpoint of material costs, labor and productivity.

The present invention provides a wavelet-based method to analyze the acoustic emission (AE) signal for online and offline identification of delamination in a CMP process. In a particular embodiment, the present invention provides a wavelet-based method to analyze the acoustic emission (AE) signal for online and offline identification of delamination of low-k dielectric layers in a copper damascene CMP process.

In a particular embodiment, the present invention provides a method of detecting a delamination defect in a chemical mechanical planarization process, the method including the steps of, sampling an acoustic emission signal of the chemical mechanical planarization process, identifying the dyadic length of the sampled acoustic emission signal, determining a maximum level of wavelet decomposition based on the dyadic length of the sampled acoustic emission signal, identifying a plurality of levels of decomposition up to the maximum level of decomposition, wavelet decomposing the sampled acoustic emission signal at each of the plurality of levels of decomposition up to the maximum level of decomposition to obtain a plurality of wavelet coefficients, identifying an energy content for each of the plurality of wavelet coefficients at each of the plurality of levels of decomposition, testing the energy content of the plurality of wavelet coefficients at each level of decomposition to identify a plurality of decomposition levels with significant wavelet coefficients having a significant energy content, thresholding the plurality of significant wavelet coefficients at the decomposition levels with significant wavelet coefficients having a significant energy content to identify a plurality of thresholded significant wavelet coefficients, reconstructing the detail signal in a time domain from each of the plurality of thresholded significant wavelet coefficients and observing the reconstructed detail signals to detect a delamination defect in the chemical mechanical planarization process.

Since most of the energy content of the acoustic emission signals is contained within the first six levels, in an additional embodiment, the step of wavelet decomposing the acoustic emission signals is limited to wavelet decomposing to six levels of decomposition.

While the system and method in accordance with the present invention may be employed both in situ or ex situ, in an additional embodiment for use in situ, the method in accordance with the present invention further includes the step of wavelet decomposing the acoustic emission signals utilizing a moving wavelet window.

To establish a standard for the wavelet based multiresolution analysis of the sampled acoustic emission signals in accordance with the present invention, an in-control sample obtained from an in-control CMP process is identified utilizing a scanning electron microscope and the acoustic emission signals obtained from the in-control sample are used to establish a standard for the based multiresolution analysis of the sampled acoustic emission signals of the wafer in question. In an exemplary embodiment, the standard established is a threshold standard.

In an exemplary embodiment of a system in accordance with the present invention, an acoustic transducer is positioned proximate to a contact region between a wafer and a polishing pad of the chemical mechanical planarization process. The acoustic transducer is used to sample acoustic emission signals associated with at least one preselected frequency or preselected frequency band and an analyzer is used to perform wavelet based multiresolution analysis of the sampled acoustic emission signals to detect a delamination defect in the chemical mechanical planarization process.

In an additional embodiment, the analyzer further includes a wavelet decomposer to decompose the acoustic emission signals, an energy identifier coupled to the wavelet decomposer-the energy identifier to identify an energy content for each of the plurality of wavelet coefficients at each level of decomposition; an energy tester coupled to the energy identifier, the energy tester to test the energy content of each level of decomposition-the energy tester to identify a plurality of levels with significant wavelet coefficients having a significant energy content; a thresholder to apply thresholds to a plurality of wavelet coefficients of the decomposed acoustic emission signals at the levels having a significant energy content, a reconstructor to reconstruct the details from the thresholded wavelet coefficients in the time domain at each of the levels having a significant energy content and a detector to observe the details of the reconstruction to detect a delamination defect in the chemical mechanical planarization process.

The system as described may be employed ex situ. Additionally, an in situ system is within the scope of the present invention utilizing a moving wavelet window.

As such, the present invention presents a novel application of a wavelet-based multiscale method in a nanomachining process chemical mechanical planarization (CMP) of wafer fabrication. The application involves identification of delamination defects of low-k dielectric layers by analyzing the nonstationary acoustic emission (AE) signal signal collected during copper damascene (Cu-low k) CMP process. An offline strategy and a moving window-based strategy for online implementation of the wavelet monitoring approach are provided. The results show that the wavelet-based approach using the AE signal offers an efficient means for real-time detection of delamination defects in CMP processes. Such an online strategy, in contrast to the existing offline approaches, offers a viable tool for CMP process control.

The present invention detects delamination during the fabrication process, through analysis of online sensor data. The wavelet based multiresolution analysis method in accordance with the present invention is used in the process of sensor data analysis. The present invention benefits the semiconductor manufacturing industry by reducing quality losses, increasing productivity, reducing the need for expensive metrology and reducing the dependence and cost of final inspection of the wafers.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
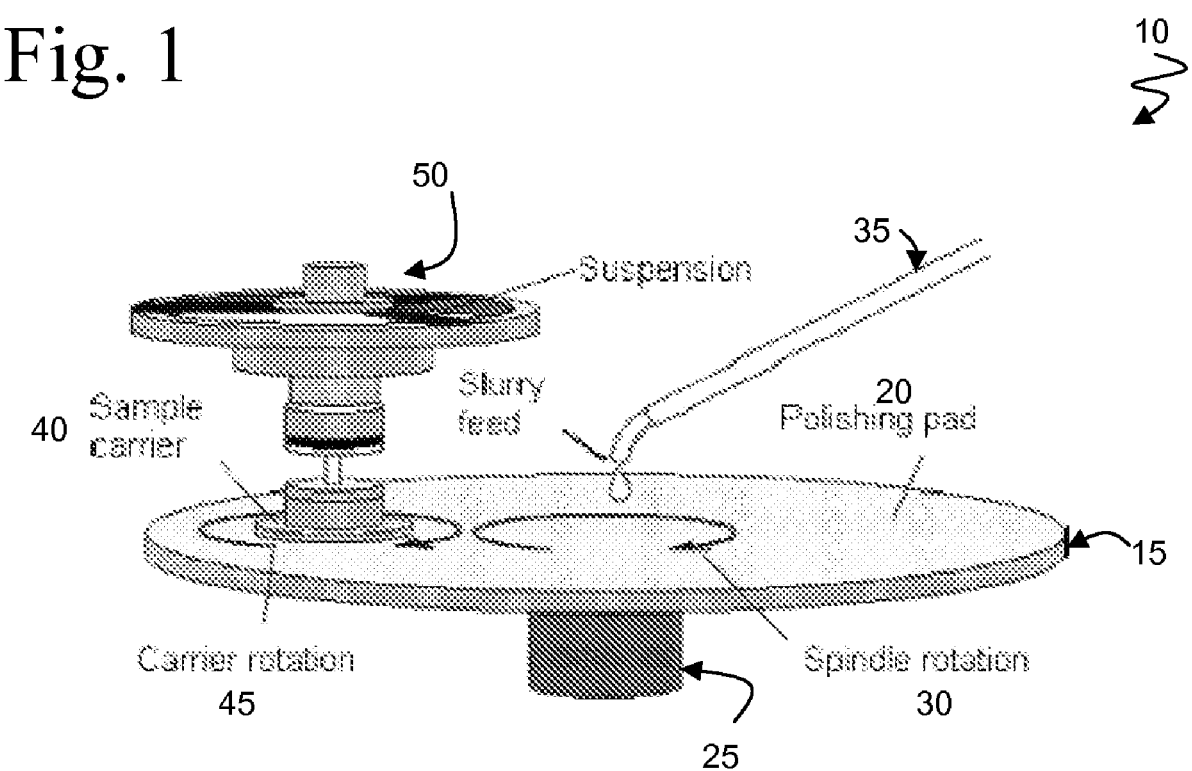
FIG. 1 is a schematic diagram of the CMP process in accordance with the present invention.

The chemical mechanical planarization process has been made more challenging in recent years due to the complex wafer topographies and the introduction of copper (instead of aluminum) and low-k dielectrics. The multilevel metallization process typically consists of etching, deposition, and planarization using a copper Damascene process. FIG. 1 illustrates a CMP setup in accordance with the present invention, which synergistically combines both tribological (abrasion) and chemical (etching) effects to achieve planarization. With reference to FIG. 1, the wafer polisher 10 includes a polishing platen 15 to which a polishing pad 20 is affixed. Polishing platen 15 includes a connection 25 to a drive mechanism (not shown) which enables the platen 15 and pad 20 to be rotated in at least one rotational direction 30. A conduit 35 dispenses a polishing slurry, typically silica or alumina abrasive particles suspended in either a basic or an acidic solution, onto polishing pad 20.

A sample carrier 40 holds a wafer to be polished. The sample carrier 40 includes a connection to one or more drive mechanisms 50 which enable the sample carrier to be selectively lowered until the wafer contacts the polishing pad 20 with a desired amount of force, rotated in at least one rotational direction 45.

The material removal rate (MRR) in CMP is usually in the range of 100-800 nm/min in thickness. A number of theories exist that attempt to characterize the exact mechanism of material removal. The process of material removal can result in a variety of defects. The use of low-k dielectrics in wafers helps to reduce the capacitance, as the gaps between the metal lines diminish due to shrinking chip size and increasing complexity. Also, current industry practice is to include a multifilm barrier between copper and dielectric and between subsequent dielectric levels to prevent the diffusion of copper into the dielectric. Low-k dielectric materials currently being considered are generally porous in nature, which results in lower values of hardness, mechanical strength, cohesive force, and modulus of elasticity. They also have poor adhesion to metals in multilevel stacks, which are partly addressed by the barrier between copper and dielectric. The above properties combined with the loading forces and rotation rates of the CMP process often lead to a common defect called delamination. Delamination can occur due to: 1) breakdown of the low-k materials; 2) failure of cap layer and low-k interface; 3) failure of low-k dielectric and underneath material interface; 4) separation of barrier/dielectric from the side of trenches; and 5) failure between metal levels in a multilevel metallization (MLM) stack. Some other examples of defects include dishing, over- and under-polishing, and lack of planarity of the wafer surface.

Wavelet-based multiresolution analysis techniques are known in the art for the analysis of both stationary and nonstationary signals. These methods provide excellent time-frequency localized information, which is achieved by varying the aspect ratio. Hence, time and frequency localized features are analyzed simultaneously with high resolution and the scheme is more adaptable to transient signals.

The basic idea behind signal processing with wavelets is that the signal can be decomposed into its constituent elements through the use of basis functions. These basis functions can be obtained from the scaled (dilated) and shifted (translated) versions of the mother wavelet (w). The wavelet analysis uses linear combinations of basis functions (wavelets), localized both in time and frequency, to represent any function in the space. For example:

$$f(t) = \sum_{j=-\infty}^{\infty} \sum_{k=-\infty}^{\infty} b_{j,k} \omega_{j,k}(t), \quad j,k \in Z$$

where j and k are dilation (or scale) and translation indexes, respectively $w_{j,k}$, denotes a collection of basis functions, and $b_{j,k}$ are the coefficients of these functions. The wavelet basis functions can also be derived from the dilation and translation ($\Phi$) of scaling functions that span the $L^2(R)$ subspace. By combining the scaling and the wavelet functions, we can represent any class of signals in $L^2(R)$ as:

$$f(t) = \sum_{k=-\infty}^{\infty} c_{j_0,k} \phi(t-k) + \sum_{k=-\infty}^{\infty} \sum_{j=j_0}^{\infty} d_{j,k} \omega(2^j t - k)$$

and where $C_{j0,k}$ and $d_{j,k}$ are coefficients for the scaling and wavelet functions, respectively. They are also called the discrete wavelet transform (DWT) of the function $f(t)$, and it is customary to start with $j_0=0$. If the wavelet system is orthogonal, then the coefficients can be calculated by:

$$c_{j_0,k} = <f(t), \phi_{j_0,k}(t)> = \int f(t)\phi_{j_0,k}(t)dt$$

$$d_{j,k} = <f(t), \omega_{j,k}(t)> = \int f(t)\omega_{j,k}(t)dt$$

If the signal is smooth, the coefficients are small in magnitude. However, if there is a jump in the signal, the magnitude of the coefficients will show a significant increase. The abrupt change in a process can be detected using the extrema of the wavelet coefficients.

Figure 2:
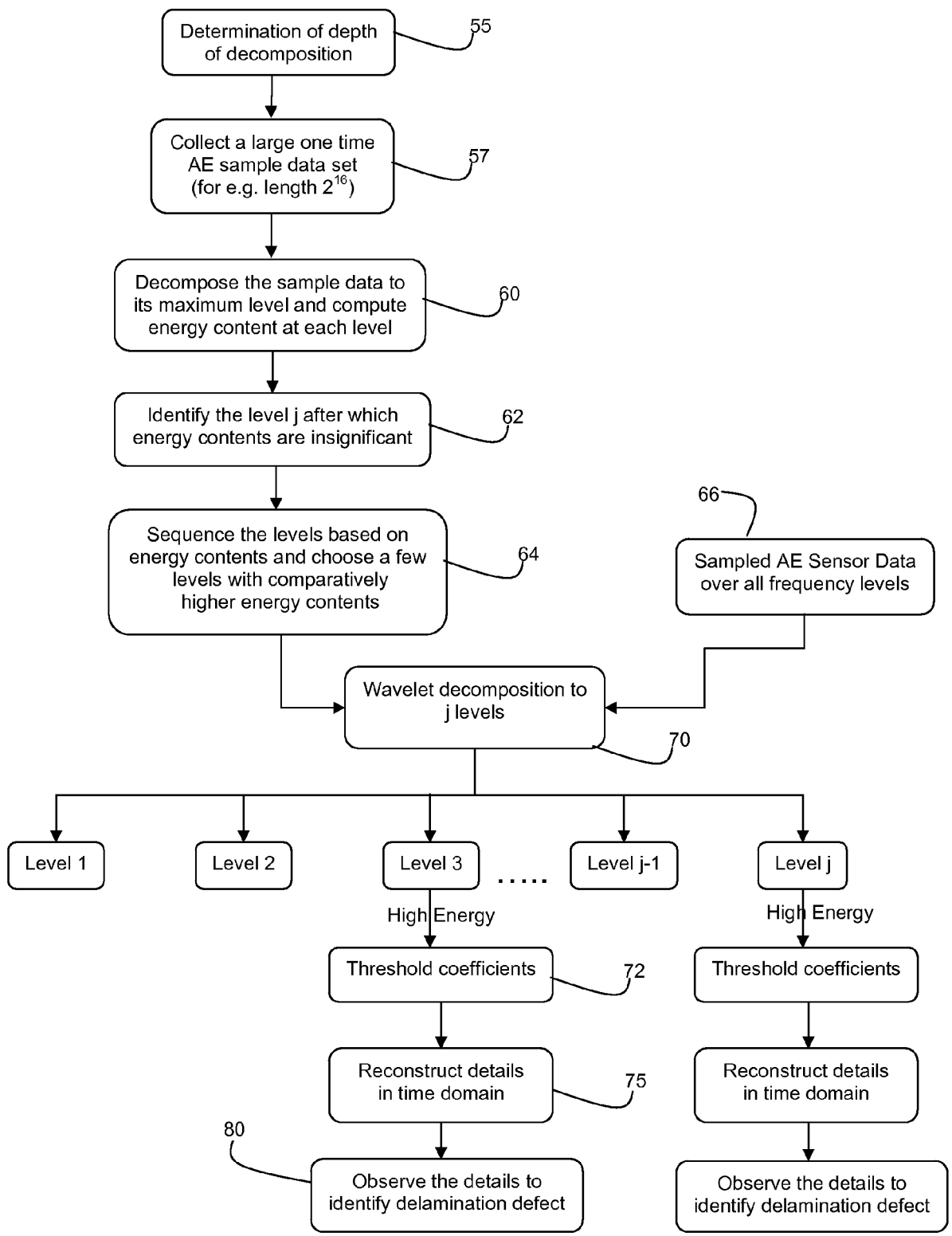
FIG. 2 is a flow diagram illustrating a detailed defect detection method in accordance with the present invention.

With reference to the flow diagram of FIG. 2, in an exemplary embodiment of the present invention a method of detecting a delamination defect in a chemical mechanical planarization process, the method including the steps of determining an appropriate depth of decomposition to be performed 55 from a large sampling of acoustic emission data from the chemical mechanical planarization process for both in-control and out-of-control data 57, decomposing the sampled acoustic emission signals to the determined level of decomposition to identify a plurality of wavelet coefficients of the acoustic emission signals and determining the energy level of the plurality of wavelet coefficients 60, identifying an energy level below which the wavelet coefficients are insignificant 62, identifying a plurality of wavelet coefficients that are significant based upon their comparatively higher energy content 64. Based upon the decomposition depth and significant energy level identified above, sampled acoustic emission data from the chemical mechanical planarization process are gathered 66, wavelet decomposed 70, and thresholding is performed on the significant wavelet coefficients 72. The details from the thresholded significant wavelet coefficients are then reconstructed in the time domain 75 and the details of the reconstruction are observed to detect a delamination defect in the chemical mechanical planarization process 80.

The following is an exemplary embodiment and is not intended to limit the scope of the present invention. In an exemplary embodiment of the present invention, experimental setups and process conditions under which text data were collected is provided. Two chemical mechanical planarization test beds were used for data collection. Both test beds were equipped with AE sensors and necessary data acquisition systems. Several wafers were planarized under different combinations of rotational speed (r/min) and downward pressure (psi) while maintaining the same slurry composition, wafer type, and pad materials. A first set of wafers was polished using rotational speeds of 100, 150, 200, and 250 r/min, under constant downward pressure of 3 psi. Subsequently, more wafers were polished using downward pressures of 2, 4, and 6 psi while maintaining a constant rotational speed of 152 r/min. In each wafer polishing trial, AE data was collected. In this exemplary embodiment, the type of wafer used was a patterned copper wafer backed with low-k dielectric material, and the polishing pad used was of type IC 1000/SUBA IV. The sampled AE signals were band passed using low- and high-frequency Buttersworth filters before further analysis in order to eliminate contamination at the two extreme ends (low and high) of the frequency spectrum. The polished wafers were examined using SEM for delamination defects. The wafers that showed presence of only delamination defects were chosen for further data analysis. These data sets were identified as out-of-control data sets and were classified into three categories (moderately bad, bad, and worse) based on the severity of the delamination defects. Also collected were samples from wafers with no defects at all. These samples were referred to as in-control data.

Figure 3:
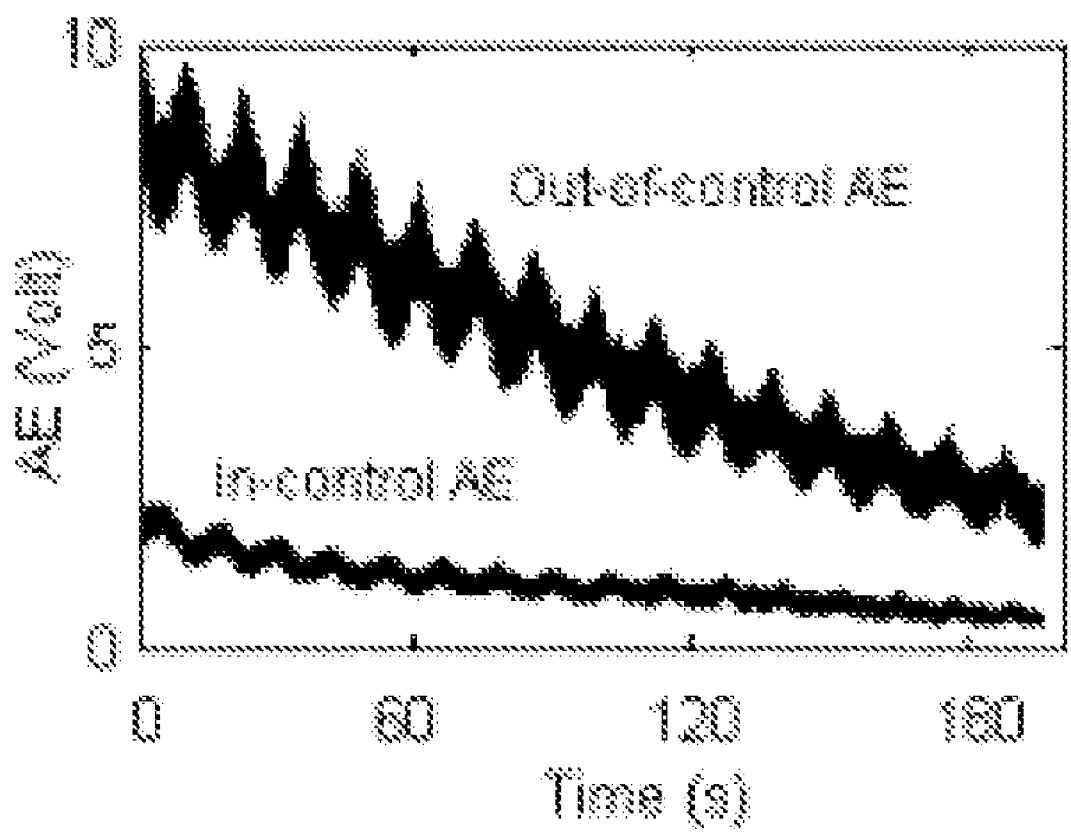
FIG. 3 is an illustrative view of raw data plots of in-control and out-of-control AE signals at 152 r/min and 2psi downward pressure in accordance with a particular embodiment of the present invention.

FIG. 3 shows raw data plots of in-control and out-of-control AE signals collected at 152 r/min of the sample carrier and 2 psi downward pressure on the wafer. The wavelet-based multiresolution analysis method, presented later, was then applied on these data sets to assess the efficacy of the detection approach.

The plots of raw data sets clearly indicate that AE signals are nonstationary since their mean values change over time. A sample of these plots for data representing severe delamination is shown in FIG. 3. Several other observations that were made from the plots are as follows: 1) Though it can be observed that the out-of-control signals have higher amplitudes than the corresponding in-control signals, this difference is not always evident for data representing minor delamination. Other than in extreme cases, the plots of the in-control and the out-of-control signals do not provide sufficient indication that could be used to assess the presence of any delamination defect. Presence of noise in the data further conceals the difference.

Hence, robust statistical procedures are needed to efficiently denoise the data and extract its time-frequency related features. 2) As the CMP process progresses, the amplitude of the AE signal tends to decrease indicating the extent of polishing. 3) The data sets were analyzed for the type of noise and the presence of autocorrelation. It was found that AE signals are corrupted with white noise and are highly autocorrelated. The white noise is generated from sources like machine vibrations, thermal agitation during polishing, and electron movements during signal transmission. 4) The data sets, when processed with the build-in denoising tool of the CMP data acquisition system, showed that the process is unstable initially for up to 7 s. This instability may be attributed to the removal of the oxide layers formed by atmospheric oxidation and the gradual revolution per minute increase until a steady rotational speed is reached.

In accordance with the present invention, a multiresolution analysis procedure for the detection of delamination defects in chemical mechanical planarization process for use in an offline setting is presented. The AE signals are analyzed to assess their wavelet coefficient properties, such as autocorrelation, normality, size, and energy content. Though all the data sets are within the scope of the present invention, the results pertaining to 152 r/min and 2 psi downward pressure are presented as follows.

Since the in-control data is used in establishing the standards (such as threshold limits) for the detection approach, this data collected after 7 s of initial instability was prescreened to eliminate outliers as follows. Due to the nonstationary nature of the data, prescreening of outliers was done using short data segments of length 500 and by applying three sigma limits. Any data outside of the limits were considered outliers and removed. The prescreening procedure eliminated at most 1 outlier for every 500 points, and the original data was literally preserved. The longest possible dyadic length of the data was selected from the prescreened data. A data length of 2 was chosen. A similar length for the out-of-control data was also chosen after discarding data for the first 7 s. Both in-control and out-of-control AE data were then decomposed separately into 16 levels using Daubechies fourth-order wavelet basis functions, resulting in the wavelet and scaling function coefficients. The number of levels select and the use of Daubechies fourth-order wavelet basis function is exemplary and is not meant to be a limiting factor of the invention. The selection of the basis function was motivated by the following properties. 1) It has orthogonal basis with a compact support. 2) The coefficients of the basis function add up to $\sqrt{2}$, and their sum of squares is unity; this property is critical for perfect reconstruction. 3) The coefficients are orthogonal to their double shifts. 4) The frequency response has a double zero (produces two vanishing moments) at the highest frequency, which provides maximum flatness. 5) With downsampling by two, this basis function yields a half-band filter.

Figure 4:
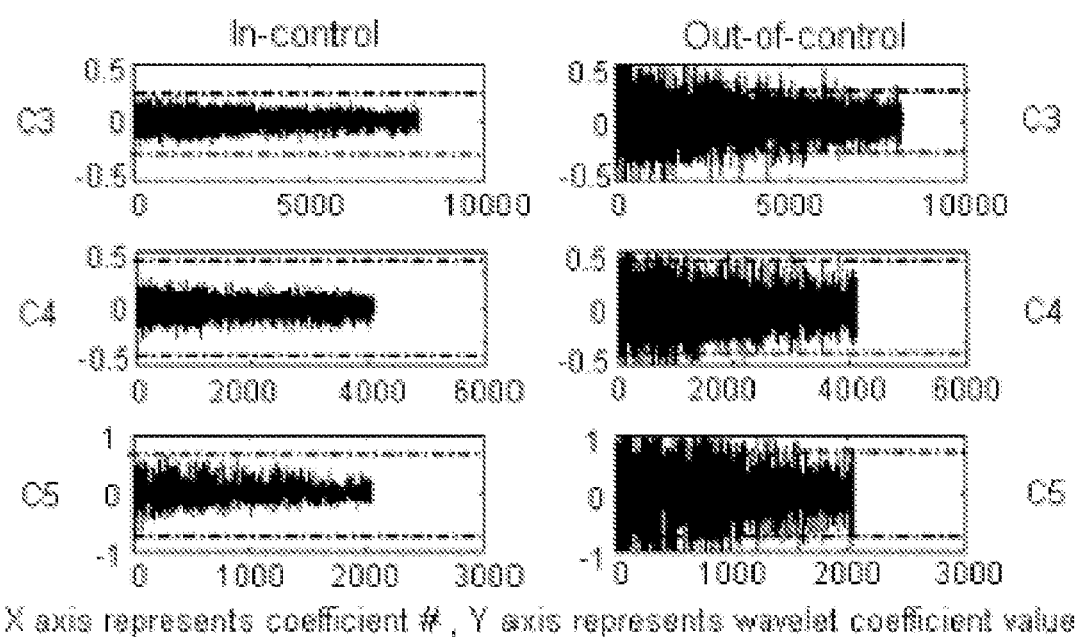
FIG. 4 is an illustrative view of the wavelet coefficients and threshold limits of the in-control and out-of-control AE signal for selected levels of decomposition.

Autocorrelation and probability distribution of the wavelet coefficients were obtained. They were found to be decorrelated and Gaussian distributed at all levels. This confirms the well-known fact that dyadic discretization (wavelet decomposition with downsampling by two) yields uncorrelated and Gaussian distributed coefficients even with highly autocorrelated and nonGaussian data A visual comparison of the wavelet coefficients for each of the scales indicates that the coefficients of the out-of-control data are generally larger than the in-control data for AE signals. However, due to the presence of noise, no formal conclusions can be made from such visual observations. Plots of the coefficients for AE and data at levels 3, 4, and 5 are shown in FIG. 4. These coefficients must be thresholded to extract the significant coefficients. Thresholding also serves the purpose of denoising if the original data is noisy.

After thresholding the coefficients, it is required to reconstruct the details in the time domain from the thresholded wavelet coefficients. This reconstruction is needed to pinpoint the exact locations of defect occurrences. In a particular embodiment of the present invention, denoising of both in-control and out-of-control coefficients were carried out using thresholds derived from in-control data using the threshold rule of Donoho et al. This threshold rule is also called visual shrink or "VisuShrink" method in which a universal scale dependent threshold is proposed. For wavelet filtering, this threshold is obtained as:

$$t_j = \sigma_j \sqrt{2\log(n)}$$

where n is the signal length and where $\sigma_j$ is the standard deviation of the coefficients at scale j. The value of $\sigma_j$ is estimated from the median of absolute deviation (MAD) of the wavelet coefficients at scale as j as:

$$\sigma_j = \frac{1}{0.6745}\text{median}(|d_{j,k}|)$$

where $d_{j,k}$ are the wavelet coefficients. In FIG. 4, the threshold limits are shown as dotted lines. The significant wavelet coefficients that fall outside of the threshold limits are then extracted by applying either soft or hard thresholding. At scale j, the thresholded coefficients are determined as follows:

Soft thresholding is:

$$\left\{\tilde{d}_{j,k} = \begin{array}{ll} \text{sign}(d_{j,k})(|d_{j,k}|-t), & |d_{j,k}| \geq t \\ 0, & |d_{j,k}| < t \end{array}\right.$$

where sign $(d_{j,k})$ is the positive or negative sign of the wavelet coefficient $d_{j,k}$.

Figure 5:
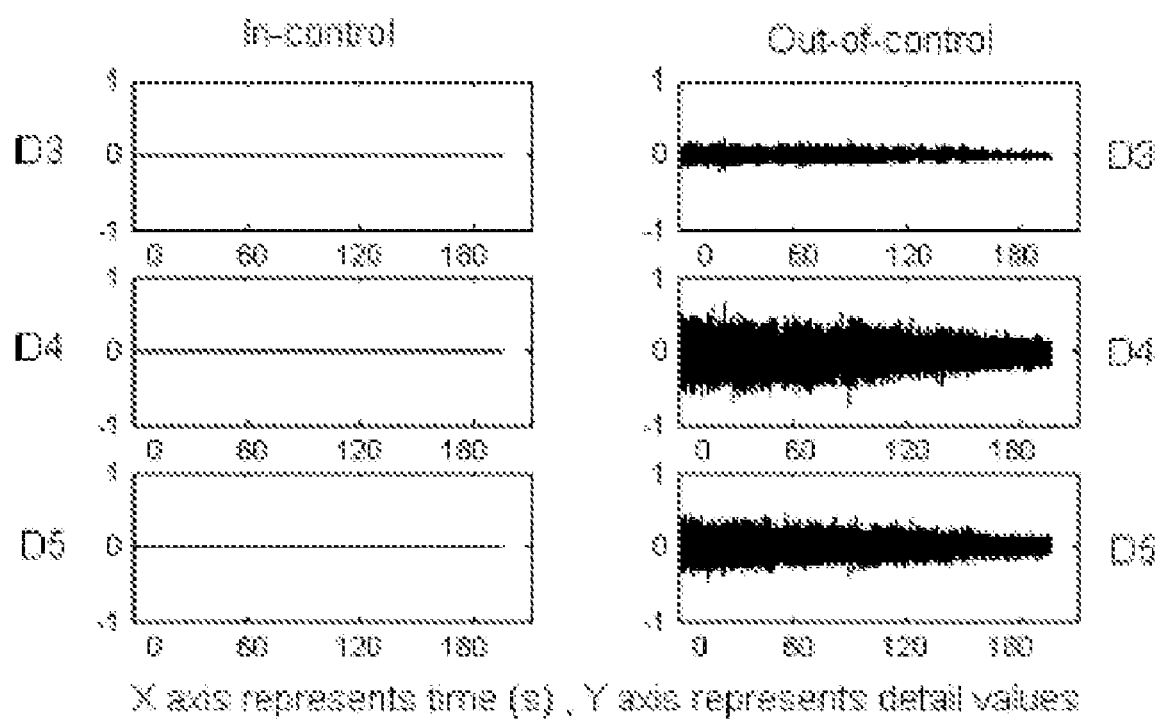
FIG. 5 is an illustrative view of the reconstructed details from offline analysis of the in-control and out-of-control AE data in accordance with an embodiment of the present invention.

The details in the time domain for each level were then calculated from the thresholded wavelet coefficients. The first two levels of the details were regarded as the high-frequency noise. In levels 3 and above, for in-control AE signals, no details were present, since all the wavelet coefficients were thresholded. This is depicted for AE signal in FIG. 5, which shows zero detail values for in-control data. However, significant values of the details were noticed for the out-of-control AE signal confirming the presence of the delamination defect as shown in FIG. 5.

Figure 6:
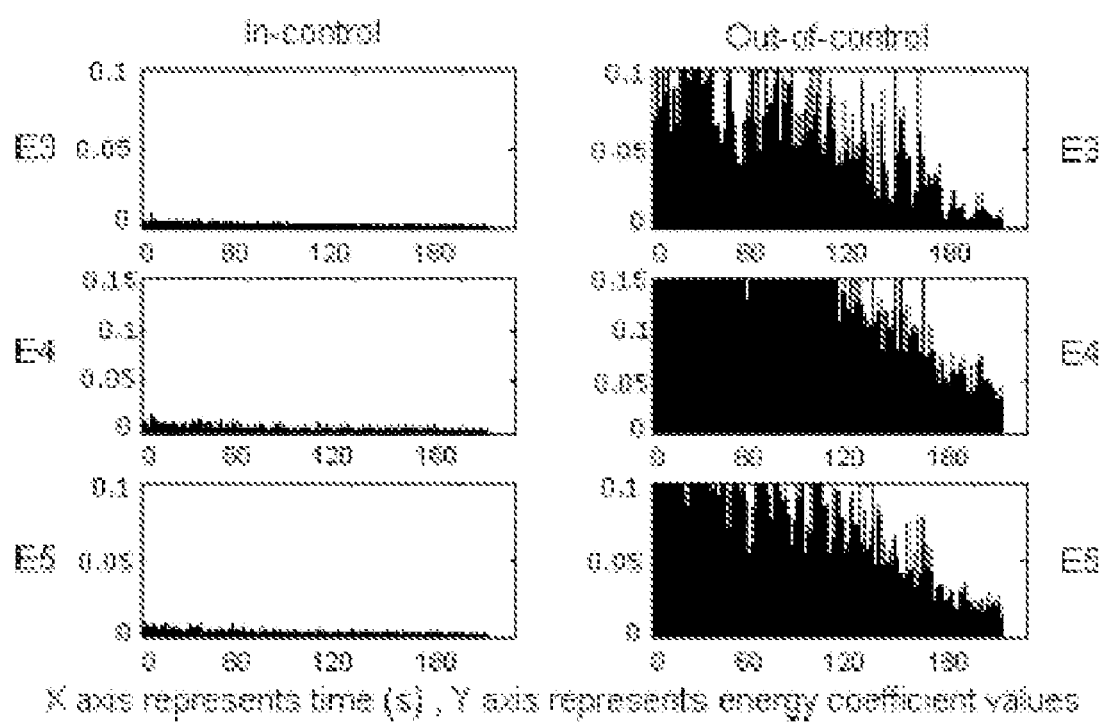
FIG. 6 is an illustrative view of the energy from offline analysis of the in-control and out-of-control AE data.
Figure 7:
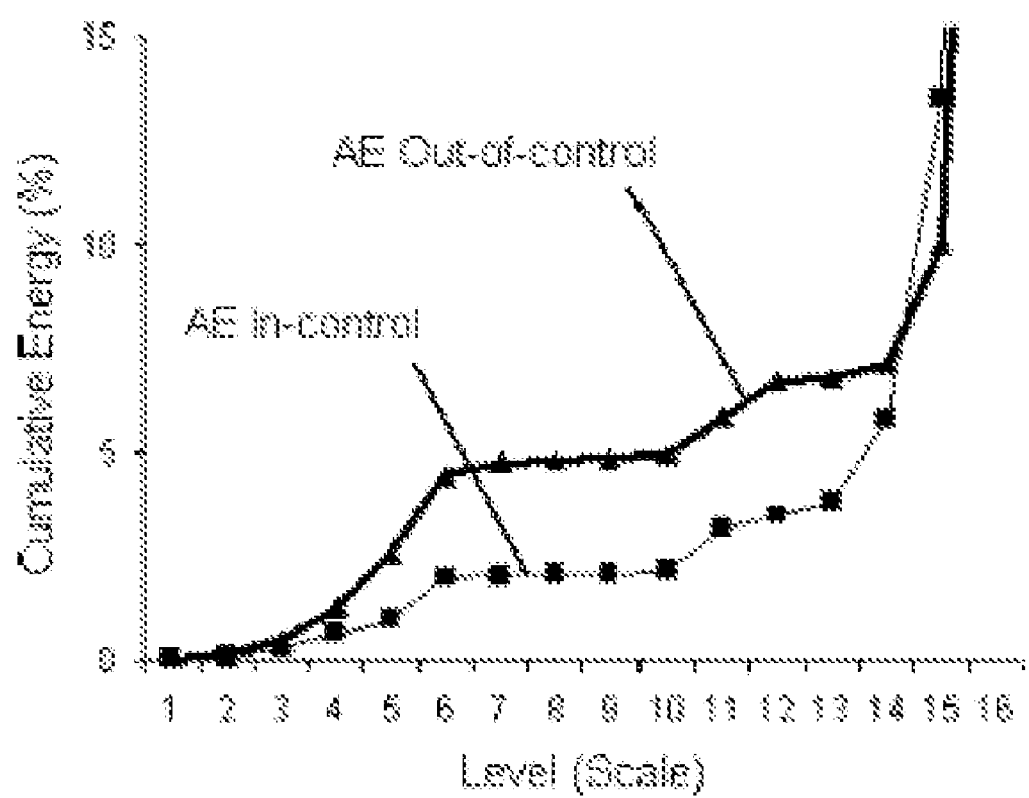
FIG. 7 is an illustrative view of the cumulative energy for in-control and out-of-control AE signals.

The energy content of the details can be used in many multiresolution applications as an indicator of process conditions. In accordance with the present invention energy at all levels were obtained by squaring the details derived from the unthresholded wavelet coefficients. FIG. 6 shows that the energy content of the out-of-control signal is significantly higher than the in-control signal indicating the presence of severe delamination. The total energy values were also obtained at all 16 levels of decomposition. FIG. 7 shows the plots of the cumulative energy at each level expressed in percentage for the in-control and out-of-control AE data. It can be seen that the cumulative out-of-control energy is greater than the in-control energy. Also, the energy of the details increases significantly up to level 6 and remains fairly constant thereafter. The rise in energy shown in the last few levels is usually ignored in analysis since these levels have only a few coefficients and contain very little process information. The above information suggests that multiresolution analysis could be restricted to six levels of decomposition.

Based on the multiresolution study presented thus far, the following conclusions were made: 1) energy and details of the AE signal at each level are good indicators for detecting the presence of delamination defect; and 3) most of the energy content of the AE signal is contained within the first six levels and, hence, multiresolution analysis can be restricted to six levels of decomposition.

This exemplary embodiment presented above was repeated for all other data sets. Observations that were made are similar to those obtained from analyzing data collected at 152 r/min and 2 psi downward pressure and, therefore, are not presented here. The computer code for the analysis was written in MATLAB (version 6.1 release 12.1) using wavelet toolbox functions.

In the particular embodiment of the present described above, an offline analysis was presented by selecting the longest possible dyadic length ($2^{16}$) of the data and performing wavelet decomposition for the entire data length simultaneously. As a consequence of high-computational needs for such a large data length, wavelet decomposition and energy analysis were done for one level at a time. The dyadic discretization (wavelet decomposition with down-sampling by two) introduces a time delay in the computation of the coefficients at nondyadic locations, and this problem is severe at coarser scales. While this methodology is useful for offline analysis of the CMP process, it is additionally evident that an online approach that overcomes the time delay and implements continuing defect identification during the process would be advantageous.

Figure 8:
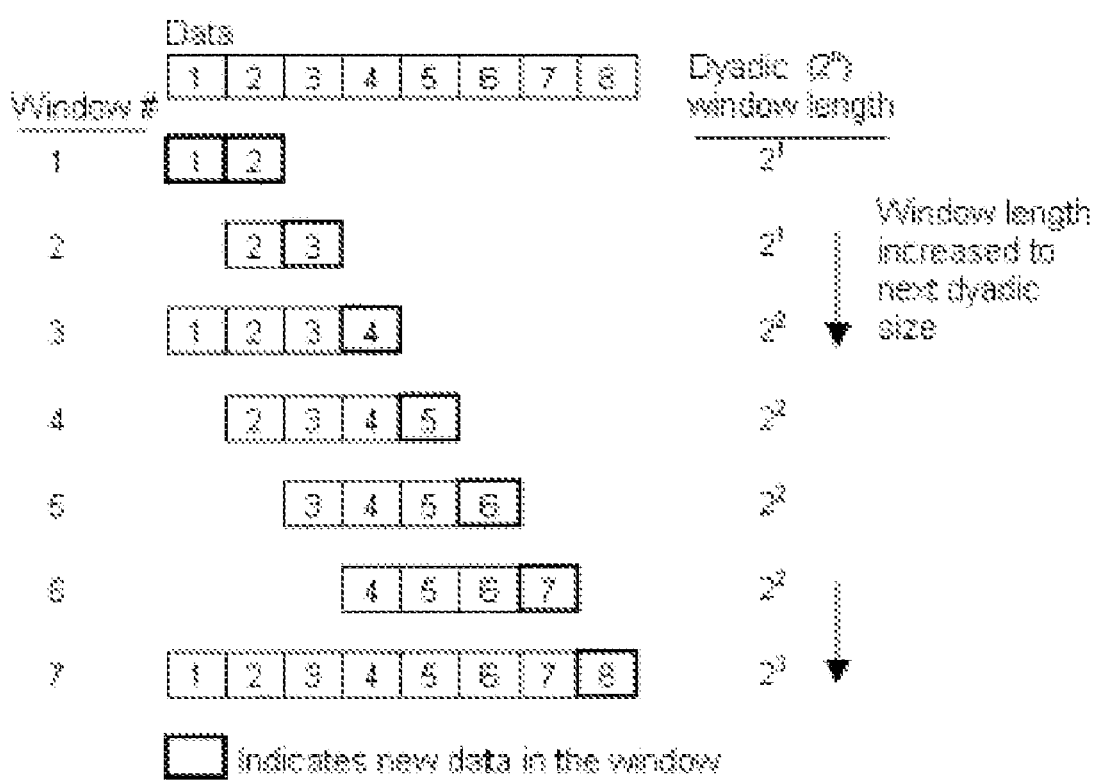
FIG. 8 is an illustrative view of the moving window concept in accordance with the present invention.

Accordingly, in an additional embodiment of the present invention, an online approach to delamination defect detection in the CMP process is presented. In the offline process previously presented, the entire length ($2^{16}$) of the AE signals were examined through one set of wavelet decomposition for each frequency level. As a result, delamination defects were correctly identified, but only after the CMP process was completed and the entire data length was available. Though such offline analysis is useful, it would also be advantageous to have a method that can detect the delamination defect during the process (i.e., online). Such an online method may present significant opportunities to resolve the problem earlier through control strategies. Thus, the motivation is evident to seek a strategy that can detect delamination using smaller segments of the data as they are being generated during the process. A moving window approach was adopted as follows. A smaller dyadic length of the window is initially chosen. As the CMP progresses and the generated data length equals the selected window width, the analysis begins. Wavelet decomposition is done for the data in the window and the resulting wavelet coefficients at each scale are soft thresholded. The threshold values used in this method are obtained from the in-control data analyzed in an offline mode. Next, the details in the time domain are reconstructed from the thresholded wavelet coefficients. In this first window, all details for each scale are checked for the presence of delamination. At this time, the window is moved to include the next data point. However, the first data point of the window is dropped to maintain the window length. This ensures dyadic length. Wavelet decomposition, thresholding, and detail reconstruction is done for the data in the new window and only the last detail value at each scale, that contains information about the most recent data point in the window, is checked for signs of delamination. The rest of the details in the new window do not contain any new information and are ignored. This process of moving the window of chosen initial dyadic length ($2^k$), k=1, 2, . . . continues until the total data length starting from the beginning reaches a length of ($2^{k+1}$). At this time, the window length is increased to ($2^{k+1}$) and the procedure continues. Upgrading of the window length is carried out until a desired length, depending on the required depth of decomposition, is reached. From this point on, the window length is kept constant. This method is called integer or uniform discretization. A schematic of the moving window concept with an initial window width of two is given in FIG. 8. To test the efficacy of the above moving window strategy to detect delamination, it was applied on the same data sets on which offline analysis was done. The results obtained were similar to those of the offline study. In the moving window procedure, the wavelet coefficients are no longer orthonormal to each other and autocorrelation between the coefficients gradually increases with increase in scale. However, as explained in the next section, the increased autocorrelation at higher scales does not affect the method. The results of the moving window strategy are presented next.

Figure 9:
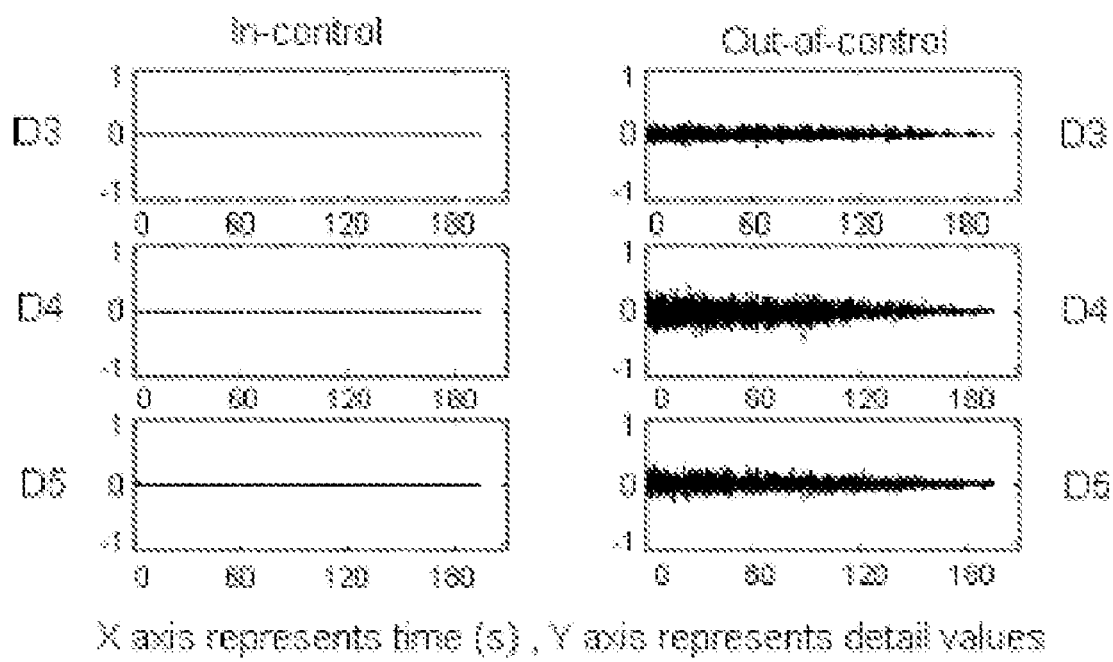
FIG. 9 is an illustrative view of the reconstructed details from online analysis of the in-control and out-of-control AE data.
Figure 10:
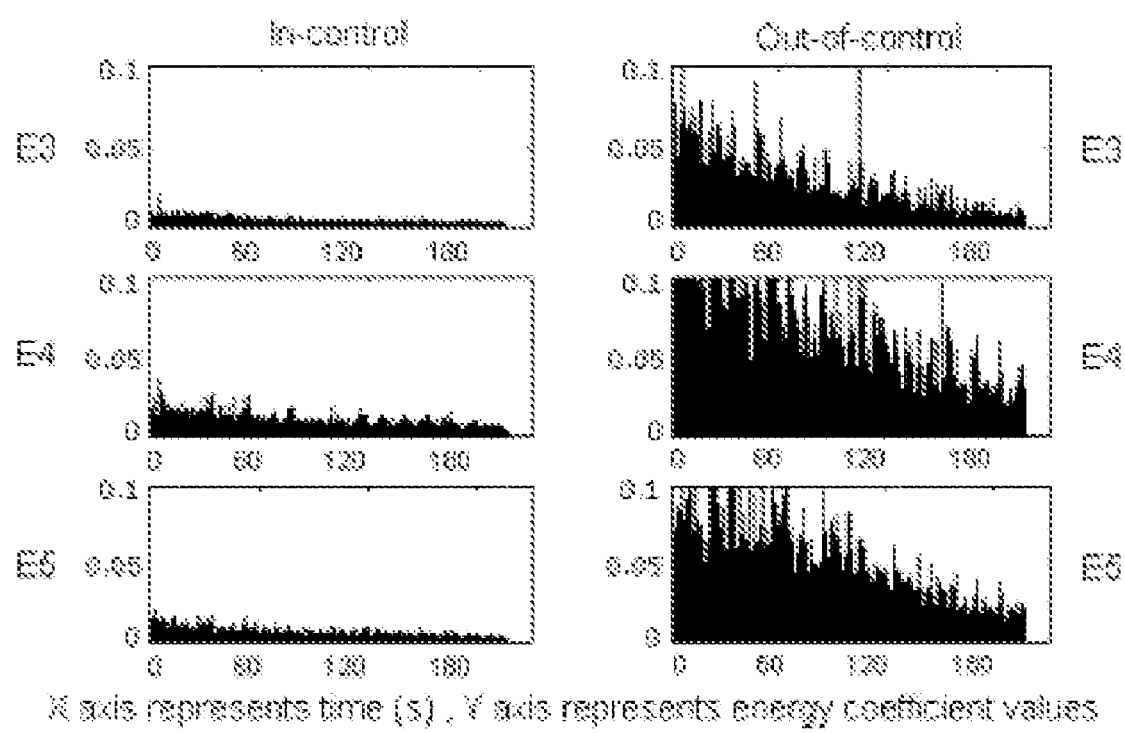
FIG. 10 is an illustrative view of the energy from online analysis of the in-control and out-of-control AE data.

In an exemplary embodiment, the moving window strategy was implemented with an initial window length of $2^6$ and a final length of $2^8$. The choice of final window length of $2^8$ was motivated by the desire to obtain eight levels of decomposition. Though offline energy analysis revealed that decomposition up to level 6 is sufficient, it is desirable to ensure that energy at levels beyond 6 are insignificant for moving window strategy as well. Wavelet decomposition in the moving window was done using Daubechies fourth-order wavelet. To illustrate the results, a comparison of the details at levels 3-5 for the in-control and out-of-control AE data is shown in FIG. 9. It is well known that levels 1 and 2 represent high-frequency noise. For the CMP data, information contained beyond level 6 is insignificant. Hence, representative levels 3, 4, and 5 were selected and are shown in the illustrations. The in-control data presents a clear picture with no details (i.e., all coefficients were thresholded). Significant details were observed for the out-of-control data indicating the presence of delamination defect. FIG. 10 shows the plot of energy, which portrays the same trend as in FIG. 6. It was also noticed during the analysis that the moving window method failed to completely eliminate autocorrelation in the coefficients. Autocorrelation was found to increase with scale and was significant after scale 6. Since energy was significant only up to scale 6, the effect of autocorrelation due to integer discretization did not impact the analysis. The moving window method was found to be effective for all types (moderately bad, bad, and worse) of delamination defects.

When dealing with signals of finite length (as done here), border distortion (end effects) is present. However, the boarder distortion affects the scaling coefficients (not the wavelet coefficients). Since delamination is only detected in the wavelet coefficients, the method was not affected by the impact of boarder distortion.

Accordingly, the present invention provides a wavelet-based detection strategy for delamination defects of low-k dielectric layers in a copper damascene CMP process. In situ sensor signals (AE) collected from the processes with only delamination defects were analyzed using offline and online implementable strategy. Acoustic emission signals are highly sensitive to delamination defects at all levels of severity, since significant detail and energy features were found to be present. The defect detection capabilities with and without the moving window strategy were found to be similar for all data sets with different process parameter settings. Wavelet-based multiresolution analysis of AE signal provides an effective online means to detect delamination of low-k dielectric layers during CMP processes.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of detecting a delamination defect in a chemical mechanical planarization process, the method comprising the steps of:
    sampling an acoustic emission signal of the chemical mechanical planarization process;
    identifying a dyadic length of the sampled acoustic emission signal;
    determining a maximum level of wavelet decomposition based on the dyadic length of the sampled acoustic emission signal;
    identifying a plurality of levels of decomposition up to the maximum level of decomposition;
    wavelet decomposing the sampled acoustic emission signal at each of the plurality of levels of decomposition up to the maximum level of decomposition to obtain a plurality of wavelet coefficients;
    identifying an energy content for each of the plurality of wavelet coefficients at each of the plurality of levels of decomposition;
    testing the energy content of the plurality of wavelet coefficients at each level of decomposition to identify a plurality of decomposition levels with significant wavelet coefficients having a significant energy content;
    thresholding the plurality of significant wavelet coefficients at the decomposition levels with significant wavelet coefficients having a significant energy content to identify a plurality of thresholded significant wavelet coefficients;
    reconstructing a detail signal in a time domain from each of the plurality of thresholded significant wavelet coefficients; and
    observing the reconstructed detail signals to detect the delamination defect in the chemical mechanical planarization process.

2. The method of claim 1, wherein the step of thresholding the plurality of significant wavelet coefficients, further comprises identifying a threshold limit, the threshold limit derived from in-control sampled acoustic emission data using Donoho's universal threshold rule.

3. The method of claim 1, wherein the step of identifying an energy content for each of the plurality of wavelet coefficients at each level of decomposition, further comprises squaring the detail signal of each of the plurality of wavelet coefficients prior to the step of thresholding the wavelet coefficients.

4. The method of claim 1, wherein the step of wavelet decomposing the acoustic emission signal further comprises wavelet decomposing the acoustic emission signal using Daubechies fourth-order wavelet basis functions.

5. The method of claim 1, wherein the maximum level of decomposition is six levels of decomposition.

6. The method of claim 1, wherein the step of wavelet decomposing the acoustic emission signals further comprises wavelet decomposing the acoustic emission signals utilizing a moving wavelet window, the moving wavelet window having a dyadic length dependent upon the maximum level of decomposition.

7. The method of claim 1, wherein the method of detecting a delamination defect in a chemical mechanical planarization process is performed ex situ.

8. The method of claim 1, wherein the method of detecting a delamination defect in a chemical mechanical planarization process is performed in situ and the step of wavelet decomposing the acoustic emission signals further comprises wavelet decomposing the acoustic emission signals utilizing a moving wavelet window, the moving wavelet window having a dyadic length dependent upon the maximum level of decomposition.

9. A system for detecting a delamination defect in a chemical mechanical planarization process, the system comprising:
   an acoustic transducer positioned proximate to a contact region between a wafer and a polishing pad of the chemical mechanical planarization process, the acoustic transducer to sample acoustic emission signals from the chemical mechanical planarization process;
   a wavelet decomposer coupled to the transducer, the wavelet decomposer to:
      identify a dyadic length of the sampled acoustic emission signals;
      determine a maximum level of wavelet decomposition based on the dyadic length of the sampled acoustic emission signals; and
      wavelet decompose the sampled acoustic emission signals at each of a plurality of levels of decomposition up to the maximum level of decomposition to obtain a plurality of wavelet coefficients;
   an energy content identifier coupled to the wavelet decomposer, the energy identifier to identify an energy content for each of the plurality of wavelet coefficients at each level of decomposition;
   an energy tester coupled to the energy content identifier to test the energy content of each of the plurality of wavelet coefficients at each level of decomposition to identify levels of decomposition with significant wavelet coefficients having a significant energy content;
   a thresholder coupled to the energy tester, the thresholder to threshold a plurality of significant wavelet coefficients at the decomposition levels with significant wavelet coefficients having a significant energy content to identify a plurality of thresholded significant wavelet coefficients;
   a reconstructor coupled to the thresholder, the reconstructor to reconstruct a detail signal in a time domain from each of the plurality of thresholded significant wavelet coefficients; and
   a detector coupled to the reconstructor, the detector to observe the reconstructed detail signals to detect the delamination defect in the chemical mechanical planarization process.

10. The system of claim 9, wherein the wavelet decomposer utilizes a Daubechies fourth-order wavelet basis function.

11. The system of claim 9, wherein the maximum decomposition level is six levels of decomposition.

12. The system of claim 9, wherein the wavelet decomposer further comprises a moving wavelet window, the moving wavelet window having a dyadic length dependent upon a predetermined level of decomposition.

13. The system of claim 9, wherein the system for detecting a delamination defect in a chemical mechanical planarization process is operated ex situ.

14. The system of claim 9, wherein the system for detecting a delamination defect in a chemical mechanical planarization process is operated in situ and wherein the wavelet decomposer further comprises a moving wavelet window, the moving wavelet window having a dyadic length dependent upon a predetermined level of decomposition.

15. A system for detecting a delamination defect in a chemical mechanical planarization process, the system comprising:
   means for sampling acoustic emission signals from the chemical mechanical planarization process;
   means for identifying a dyadic length of the sampled acoustic emission signals;
   means for determining a maximum level of wavelet decomposition based on the dyadic length of the sampled acoustic emission signals;
   means for wavelet decomposing the sampled acoustic emission signals at each of a plurality of levels of decomposition up to the maximum level of decomposition to obtain a plurality of wavelet coefficients;
   means for identifying an energy content coupled to the means for wavelet decomposing, the means for identifying an energy content identifying an energy content for each of the plurality of wavelet coefficients at each level of decomposition;
   means for testing energy coupled to the means for identifying an energy content, the means for testing energy to test the energy content of each of the plurality of wavelet coefficients at each level of decomposition to identify levels of decomposition with significant wavelet coefficients having a significant energy content;
   means for thresholding coupled to the means for testing energy, the means for thresholding to threshold a plurality of significant wavelet coefficients at the decomposition levels with significant wavelet coefficients having a significant energy content to identify a plurality of thresholded significant wavelet coefficients;
   means for reconstructing coupled to the means for thresholding, the means for reconstructing to reconstruct a detail signal in a time domain from each of the plurality of thresholded significant wavelet coefficients; and
   means for detecting coupled to the means for reconstructing, the means for detecting to observe the reconstructed detail signals to detect the delamination defect in the chemical mechanical planarization process.

16. The system of claim 15, wherein the means for wavelet decomposing utilizes a Daubechies fourth-order wavelet basis function.

17. The system of claim 15, wherein the maximum decomposition level is six levels of decomposition.

18. The system of claim 15, wherein the means for wavelet decomposing further comprises means for applying a moving wavelet window, the moving wavelet window having a dyadic length dependent upon a predetermined level of decomposition that is identified by energy analysis.

19. The system of claim 15, wherein the system for detecting a delamination defect in a chemical mechanical planarization process is operated ex situ.

20. The system of claim 15, wherein the system for detecting a delamination defect in a chemical mechanical planarization process is operated in situ and wherein the means for wavelet decomposing further comprises means for applying a moving wavelet window, the moving wavelet window having a dyadic length dependent upon a predetermined level of decomposition.

* * * * *